US006893664B1

(12) United States Patent
Burkoth et al.

(10) Patent No.: US 6,893,664 B1
(45) Date of Patent: May 17, 2005

(54) PARTICLE DELIVERY TECHNIQUES (75) Inventors: Terry Lee Burkoth, Palo Alto, CA (US); David Francis Sarphie, Madison, WI (US); Andrew Gordon Muddle, Cambs (GB); Linda Maree Porter, The Gap (AU)

(73) Assignee: Powderject Research Limited (GB)

( * ) Notice: Subject to any disclaimer, the term of this patent is extended or adjusted under 35 U.S.C. 154(b) by 0 days.

(21) Appl. No.: 09/216,641

(22) Filed: Dec. 17, 1998

Related U.S. Application Data (63) Continuation-in-part of application No. PCT/GB97/02478, filed on Sep. 11, 1997, and a continuation-in-part of application No. PCT/GB97/01636, filed on Jun. 17, 1997.

(30) Foreign Application Priority Data

| Jun. 17, 1996 | (GB) | ............................................. 9612629 |
| Sep. 11, 1996 | (GB) | ............................................. 9619002 |

(51) Int. Cl.$^7$ ............................ A61K 9/14; A61K 9/16; A61K 47/00; A01N 25/00
(52) U.S. Cl. ........................ 424/489; 424/491; 514/773
(58) Field of Search ............................... 424/489, 491; 514/773, 44, 2; 604/68, 67, 59, 60, 70, 130, 131, 140, 143

(56) References Cited

U.S. PATENT DOCUMENTS

| 4,737,366 A | * | 4/1988 | Gergely et al. ................. 426/5 |
| 4,774,085 A | | 9/1988 | Fidler |
| 4,945,050 A | | 7/1990 | Sanford et al. |
| 5,036,006 A | | 7/1991 | Sanford et al. |
| 5,053,389 A | | 10/1991 | Balschmidt et al. |
| 5,100,792 A | * | 3/1992 | Sanford et al. .......... 435/172.1 |
| 5,120,657 A | | 6/1992 | McCabe et al. |
| 5,147,291 A | | 9/1992 | Cukier |
| 5,149,655 A | | 9/1992 | McCabe et al. |
| 5,179,022 A | | 1/1993 | Sanford et al. |
| 5,204,253 A | | 4/1993 | Sanford et al. |
| 5,371,015 A | | 12/1994 | Sanford et al. |
| 5,399,328 A | | 3/1995 | Doetsch et al. |
| 5,478,744 A | | 12/1995 | Sanford et al. |
| 5,486,364 A | * | 1/1996 | King et al. .................. 424/488 |
| 5,584,807 A | | 12/1996 | McCabe |
| 5,630,796 A | * | 5/1997 | Bellhouse et al. ............ 604/49 |
| 5,714,166 A | * | 2/1998 | Tomalia et al. ............. 424/1.33 |
| 5,865,796 A | | 2/1999 | McCabe |
| 5,899,880 A | | 5/1999 | Bellhouse et al. |
| 6,004,286 A | | 12/1999 | Bellhouse et al. |
| 6,010,478 A | * | 1/2000 | Bellhouse et al. ............ 604/70 |
| 6,013,050 A | | 1/2000 | Bellhouse et al. |
| 6,168,587 B1 | | 1/2001 | Bellhouse et al. |
| 6,194,389 B1 | * | 2/2001 | Johnston et al. ............... 514/44 |
| 6,331,310 B1 | | 12/2001 | Roser et al. |

FOREIGN PATENT DOCUMENTS

| EP | 0012740 | 6/1980 |
| EP | 0446597 A1 | 9/1991 |
| JP | 60-36326 | 2/1985 |
| JP | 2-240023 | 9/1990 |
| JP | 5-806 | 1/1993 |
| JP | 6-507396 | 8/1994 |
| WO | WO 92/04439 | 3/1992 |
| WO | WO 94/23738 | * 10/1994 |
| WO | WO 94/24263 | 10/1994 |
| WO | WO 96/04947 | 2/1996 |
| WO | WO 96/12513 | 5/1996 |
| WO | WO 96/20022 | 7/1996 |
| WO | WO 96/25190 | 8/1996 |
| WO | WO 97/34652 | 9/1997 |

OTHER PUBLICATIONS

Merriam–Webster's Dictionary, Tenth Edition, Springfield, Massachusetts, USA, 1999.*
Dang et. al.; Gene therapy and Translational Cancer Research, 1999, Clinical Cancer Research vol. 5: 471–474.*
Riddell et. al.; T–Cell mediated rejection of gene–modified HIV–specific cytotoxic T Lymphocytes in HIV–infected patients, 1996, Nature Medicine vol. 2, No. 2: 216–223.*
Palmer et. al.; Gentically modified skin fibroblasts persist long after transplantation but gradually inactiivate introduced genes, 1991, Proc. Natl. Acad. Sci., vol. 88: 1330–1334.*
W. Leitner et. al.; DNA and RNA–based vaccines: principles, progress and prospects; Elsevier Vaccine 18(2000); 765–777.*
M.J. McCluskie et. al.; Route and Method of Delivery of DNA Vaccine Influence Immune Responses in Mice and Non–Human Primates, 1999, MOlecular Medicine 5; 287–300.*
M. Chattergoon et. al.; Genetic immunizations: a new era in vaccines and immune therapeutics; Aug., 1997; The FASEB Journal vol. 11 ; 753–763.*
N. Miller et. al.; Targeted vectors for gene therapy; Feb., 1995; The FASEB Journal, vol. 9; 190–199.*

(Continued)

*Primary Examiner*—David Guzo
*Assistant Examiner*—Quang Nguyen
(74) *Attorney, Agent, or Firm*—Foley & Lardner, LLP (57) ABSTRACT

A method is provided for in vivo or ex vivo delivery of a preparation of powdered nucleic acid molecules into vertebrate tissue for transformation of cells in the tissue using needleless injection techniques. The method can be used to deliver therapeutically relevant nucleotide sequences to cells in mammalian tissue to provide gene therapy, elicit immunity or to provide antisense or ribozyme functions. A method for providing densified processed pharmaceutical compositions is also described. The method is used to convert non-dense pharmaceutical powders or particulate formulations into densified particles optimally suited for transdermal delivery using a needleless syringe. The method is also used to optimize the density and particle size of powders and particulate formulations for subsequent transdermal delivery thereof. Densified pharmaceutical compositions formed by the present methods are also provided.

12 Claims, 3 Drawing Sheets

OTHER PUBLICATIONS

M. Deonarain; Ligand–targeted receptor–mediated vectors for gene delivery; 1998 Exp. Opin. Ther. Patents 8(1): 53–69.*

I. Verma et. al.; Gene Therapy– promises, problems and prospects;1997, Nature: vol. 389 ,239–242.*

N. Wivel et. al.; Methods of Gene Delivery; Jun., 1998; Hematology/ Oncology Clinics Of NOrth America, vol. 12, 483–501.*

Hofmann et al, (1995) *Bioelectrochemistry and Bioenergetics 38*:209–222.

* cited by examiner

PARTICLE DELIVERY TECHNIQUES

CROSS-REFERENCE TO RELATED APPLICATIONS

This application is a continuation-in-part of International Patent Application Numbers PCT/GB97/01636, filed Jun. 17, 1997, and PCT/GB97/02478, filed Sep. 11, 1997, both designating the United States, from which applications priority is claimed pursuant to 35 U.S.C. §365(c) and which applications are incorporated herein by reference in their entireties.

TECHNICAL FIELD

The present invention relates generally to particle delivery methods. More particularly, the invention pertains to in vivo and ex vivo delivery of powdered nucleic acid molecules into mammalian tissue using needleless injection techniques. The invention also relates to methods for forming dense, substantially solid particles from non-dense particulate pharmaceutical compositions such as those prepared using freeze-drying or spray drying techniques. The densified compositions obtained using the method are particularly suitable for transdermal particle delivery from a needleless syringe system.

BACKGROUND OF THE INVENTION

The ability to deliver agents into and through skin surfaces (transdermal delivery) provides many advantages over oral or other parenteral delivery techniques. In particular, transdermal delivery provides a safe, convenient and non-invasive alternative to traditional drug administration systems, conveniently avoiding the major problems associated with oral delivery, e.g., variable rates of absorption and metabolism, gastrointestinal irritation and/or bitter or unpleasant drug tastes. Transdermal delivery also avoids problems associated with traditional needle and syringe delivery, e.g., needle pain, the risk of introducing infection to treated individuals, the risk of contamination or infection of health care workers caused by accidental needle-sticks and the disposal of used needles. In addition, such delivery affords a high degree of control over blood concentrations of administered drugs.

However, despite its clear advantages, transdermal drug delivery presents a number of its own inherent logistical problems. The passive delivery of drugs through intact skin necessarily entails the transport of molecules through a number of structurally different tissues, including the stratum corneum, the viable epidermis, the papillary dermis, and the capillary walls in order for the drug to gain entry into the blood or lymph system. Transdermal delivery systems must therefore be able to overcome the various resistances presented by each type of tissue. In light of the above, a number of alternatives to passive transdermal delivery have been developed. These alternatives include the use of skin penetration enhancing agents, or "permeation enhancers," to increase skin permeability, as well as non-chemical modes such as the use of iontophoresis, electroporation or ultrasound. However, such techniques often give rise to unwanted side effects, such as skin irritation or sensitization. Thus, the number of drugs that can be safely and effectively administered using traditional transdermal delivery methods has remained limited.

More recently, a novel transdermal delivery system that entails the use of a needleless syringe to fire solid drug-containing particles in controlled doses into and through intact skin has been described. In particular, commonly owned U.S. Pat. No. 5,630,796 to Bellhouse et al. describes a needleless syringe that delivers pharmaceutical particles entrained in a supersonic gas flow. The needleless syringe is used for transdermal delivery of powdered drug compounds and compositions, for delivery of genetic material into living cells (e.g., gene therapy) or nucleic acid immunization, and for the delivery of biopharmaceuticals to skin, muscle, blood or lymph. The needleless syringe can also be used in conjunction with surgery to deliver drugs and biologics to organ surfaces, solid tumors and/or to surgical cavities (e.g., tumor beds or cavities after tumor resection). In theory, practically any pharmaceutical agent that can be prepared in a substantially solid, particulate form can be safely and easily delivered using such devices.

One particular needleless syringe generally comprises an elongate tubular nozzle having a rupturable membrane initially closing the passage through the nozzle and arranged substantially adjacent to the upstream end of the nozzle. Particles of a therapeutic agent to be delivered are disposed adjacent to the rupturable membrane and are delivered using an energizing means which applies a gaseous pressure to the upstream side of the membrane sufficient to burst the membrane and produce a supersonic gas flow (entraining the pharmaceutical particles) through the nozzle for delivery from the downstream end thereof. The particles can thus be delivered from the needleless syringe at delivery velocities as high as Mach 1 to Mach 8, which velocities are readily obtainable upon the bursting of the rupturable membrane.

Another needleless syringe configuration generally includes the same elements as described above, except that instead of having the pharmaceutical particles entrained within a gas flow, the downstream end of the nozzle is provided with a diaphragm which is moveable between a resting "inverted" position (in which the diaphragm presents a concavity on the downstream face to contain the pharmaceutical particles) and an "everted" position (in which the diaphragm is outwardly convex on the downstream face as a result of a supersonic shockwave having been applied to the upstream face of the diaphragm). In this manner, the pharmaceutical particles contained within the concavity of the diaphragm are expelled at a high initial velocity from the device for transdermal delivery thereof to a targeted tissue surface.

Transdermal delivery using the above-described needleless syringe configurations is carried out with particles having an approximate size that generally ranges between 0.1 and 250 μm. For drug delivery, a typical particle size is usually at least about 10 to 15 μm (the size of a typical cell). For gene delivery, a typical particle size is generally substantially smaller than 10 μm. Particles larger than about 250 μm can also be delivered from the device, with the upper limitation being the point at which the size of the particles would cause untoward damage to the skin cells. The actual distance which the delivered particles will penetrate depends upon particle size (e.g., the nominal particle diameter assuming a roughly spherical particle geometry), particle density, the initial velocity at which the particle impacts the skin surface, and the density and kinematic viscosity of the skin. In this regard, optimal particle densities for use in needleless injection generally range between about 0.1 and 25 $g/cm^3$, preferably between about 0.8 and 1.5 $g/cm^3$, and injection velocities generally range between about 150 and 3,000 m/sec.

A particularly unique feature of the needleless syringe is the ability to optimize the depth of penetration of delivered particles, thereby allowing for targeted administration of pharmaceuticals to various sites. For example, particle characteristics and/or device operating parameters can be selected to provide for penetration depths for, inter alia, epidermal or dermal delivery. One approach entails the selection of particle size, particle density and initial velocity to provide a momentum density (e.g., particle momentum divided by particle frontal area) of between about 2 and 10 kg/sec/m, and more preferably between about 4 and 7 kg/sec/m. Such control over momentum density allows for tissue-selective delivery of the pharmaceutical particles.

Accordingly, there is a need to provide a reliable method for preparing sufficiently dense particles (having a density of about 0.8 to 1.5 $g/cm^3$) which have an average size of about 0.1 to 150 $\mu$m from a wide variety of pharmaceutical compositions. These pharmaceutical particles can thus be transdermally delivered to a subject using a needleless syringe system.

Needleless syringes, such as those described above, also provide a unique means for gene therapy and nucleic acid immunization. These techniques provide for the transfer of a desired gene into a subject with the subsequent in vivo expression thereof. Gene transfer can be accomplished by transfecting the subject's cells or tissues ex vivo and reintroducing the transformed material into the host. Alternatively, genes can be administered directly to the recipient.

A number of methods have been developed for gene delivery in these contexts. For example, viral-based systems using, e.g., retrovirus, adenovirus, and adeno-associated viral vectors, have been developed for gene delivery. However, these systems pose the risk of delivery of replication-competent viruses. Hence, nonviral methods for direct transfer of genes into recipient cells and tissues are desirable.

Nonviral methods of gene transfer often rely on mechanisms employed by mammalian cells for the uptake and intracellular transport of macromolecules. For example, receptor-mediated methods of gene transfer have been developed. The technique utilizes complexes between plasmid DNA and polypeptide ligands that can be recognized by cell surface receptors. However, data suggests that this method may permit only transient expression of genes and thus has only limited application.

Additionally, microinjection techniques have been developed for the direct injection of genetic material into cells. The technique, however, is laborious and requires single cell manipulations. Thus, the method is inappropriate for use on a large scale.

Direct injection of DNA-containing solutions into the interstitial space for subsequent uptake by cells has also been described. For example, International Publication No. WO 90/11092, published 4 Oct. 1990, describes the delivery of isolated polynucleotides to the interior of cells wherein the isolated polynucleotides are delivered into the interstitial space of the tissue and then taken up by individual cells to provide a therapeutic effect. Such methods entail the injection of the DNA-containing solutions into tissue using conventional needles or cannulas, and are therefore not well suited for long term therapies or for field or home applications.

Biolistic particle delivery systems (particle bombardment systems) have also been developed for gene delivery into plant cells. Such techniques use a "gene gun" to introduce DNA-coated microparticles, such as DNA-coated metals, into cells at high velocities. The coated metals (biolistic core carriers) are generally propelled into cells using an explosive burst of an inert gas such as helium. See, e.g., U.S. Pat. No. 5,100,792 to Sanford et al. The technique allows for the direct, intracellular delivery of small amounts of DNA.

Biolistic core carriers upon which the DNA is coated, such as tungsten, gold, platinum, ferrite, polystyrene or latex, have to date been needed to achieve adequate gene transfer frequency by such direct injection techniques. See, e.g., International Publication No. WO 94/23738, published Oct. 27, 1994. In particular, these materials have been selected based on their availability in defined particle sizes around 1 $\mu$m in diameter, as well as providing a sufficiently high density to achieve the momentum required for cell wall or cell membrane penetration. Additionally, common biolistic core carriers are chemically inert to reduce the likelihood of explosive oxidation of fine microprojectile powders, are non-reactive with DNA and other components of the precipitating mixes, and display low toxicity to target cells. See e.g., *Particle Bombardment Technology for Gene Transfer*, (1994) Yang, N. ed., Oxford University Press, New York, N.Y. pages 10–11.

However, such biolistic techniques are not appropriate for use with large DNA molecules since precipitation of such molecules onto core carriers can lead to unstable configurations which will not withstand the shear forces of gene gun delivery.

Accordingly, there remains a need to provide a highly efficient method for introducing therapeutically relevant DNA or other nucleic acid molecules into mammalian tissue cells wherein the method avoids the problems commonly encountered with prior gene delivery techniques.

DISCLOSURE OF THE INVENTION

The present invention is based on the surprising discovery that substantially solid particles of nucleic acid molecules having a nominal average diameter of at least about 0.1 $\mu$m, preferably at least about 10 $\mu$m (which are therefore larger than the average mammalian cell), can be delivered into cells of mammalian tissue without the need for biolistic core carriers. The result is unexpected because it was heretofore believed that only small DNA-coated core carrier particles, having an extremely high particle density and a much smaller size than a typical mammalian cell, could adequately be used as microprojectiles in biolistic gene delivery techniques. See e.g., *Particle Bombardment Technology for Gene Transfer*, (1994) Yang, N. ed., Oxford University Press, New York, N.Y. pages 10–11.

In the practice of the invention, powdered nucleic acid molecules are delivered using needleless injection techniques. In particular, a novel delivery system that uses a needleless syringe to fire solid particles of therapeutic agents in controlled doses into and through intact skin has recently been described in commonly owned U.S. Pat. No. 5,630, 796. The patent describes a needleless syringe that delivers pharmaceutical particles entrained in a high velocity gas flow. The needleless syringe can be used for transdermal delivery of powdered drug compounds and compositions, for delivery of genetic material into living cells (e.g., gene therapy) and for the delivery of biopharmaceuticals to skin, muscle, blood or lymph. The needleless syringe can also be used in conjunction with surgery to deliver drugs and biologics to organ surfaces, solid tumors and/or to surgical cavities (e.g., tumor beds or cavities after tumor resection).

Furthermore, the nucleic acids to be delivered can be converted from non-dense pharmaceutical powders or particulate formulations (e.g., those having particle densities below that required for transdermal delivery from a needleless syringe) into densified (compacted) particles that are optimally suited for transdermal delivery using a needleless syringe. The method is equally applicable to densification of pharmaceutical agents other than nucleic acids.

Accordingly, in one embodiment, the invention is directed to a method for delivering solid particles comprised of nucleic acid molecules to mammalian tissue for the genetic transformation of cells in the tissue with the delivered nucleic acids. In a substantial departure from conventional particle bombardment techniques, the nucleic acid particles transferred using the method of the present invention are not delivered using biolistic core carriers. Furthermore, the molecules can have a particle size that is equal to or larger than the average mammalian cell size.

More particularly, densified particles comprised of selected nucleic acid molecules and, optionally, suitable vehicles or excipients, are prepared for delivery to mammalian tissue via a needleless syringe which is capable of expelling the particles at delivery velocities approaching Mach 1 to Mach 8 speeds. The particles have an average size that is at least about 0.1 $\mu$m, wherein an optimal particle size is usually at least about 10 to 15 $\mu$m (equal to or larger than the size of a typical mammalian cell). However, nucleic acid particles having average particle sizes of 250 $\mu$m or greater can also be delivered using the present method. The depth that the delivered particles will penetrate the targeted tissue depends upon particle size (e.g., the nominal particle diameter assuming a roughly spherical particle geometry), particle density, the initial velocity at which the particle impacts the tissue surface, and the density and kinematic viscosity of the tissue. In this regard, optimal individual particle densities (e.g., in contrast to bulk powder density) for use in needleless injection generally range between about 0.1 and 25 g/cm$^3$, and injection velocities generally range between about 150 and 3,000 m/sec.

In various aspects of the invention, the above method can be practiced in vivo to provide targeted delivery of the nucleic acid particles to a target tissue, such as delivery to the epidermis (for gene therapy applications) or to the stratum basal layer of skin (for nucleic acid immunization applications). In these aspects of the invention, particle characteristics and/or device operating parameters are selected to provide optimal tissue-specific delivery. One particular approach entails the selection of particle size, particle density and initial velocity to provide a momentum density (e.g., particle momentum divided by particle frontal area) of between about 2 and 10 kg/sec/m, and more preferably between about 4 and 7 kg/sec/m. Such control over momentum density allows for precisely controlled, tissue-selective delivery of the nucleic acid particles.

In other aspects of the invention, the needleless syringe is used to transfect cells or tissues ex vivo with the particulate nucleic acid molecules, wherein the transformed cells are subsequently reintroduced into the host.

In another embodiment of the invention, a method is provided for converting non-dense pharmaceutical powders or particulate formulations (e.g., having density characteristics below that required for transdermal delivery from a needleless syringe) into densified (compacted) particles that are optimally suited for transdermal delivery using a needleless syringe. Such particles have an optimal particle density ranging from about 0.1 to about 25 g/cm$^3$, preferably ranging from about 0.5 to about 3.0 g/cm$^3$, and most preferably ranging from about 0.8 to about 1.5 g/cm$^3$. The densified particles are processed to obtain optimal particle sizes ranging from about 0.1 to about 250 $\mu$m, preferably ranging from about 0.1 to about 150 $\mu$m, and most preferably ranging from about 20 to about 60 $\mu$m. The method entails the compaction of a pharmaceutical composition using high pressure and, optionally vacuum, to densify the composition. The resulting compacted material is then size-reduced using conventional methods to provide densified particles of optimized size.

In a related embodiment of the invention, a method is provided for optimizing the density and particle size of a particulate pharmaceutical composition that has particle size and density characteristics that fall within the above ranges. These particles are rendered more suitable for needleless syringe delivery using the above-described compaction and size-reduction techniques. In this manner, the penetration depths that are obtained when the optimized particles are delivered using a needleless syringe can be adjusted to provide targeted dermal or intra-dermal delivery.

In a further related embodiment, the invention pertains to a method for optimizing the particle size and density of a lyophilized or spray-dried biopharmaceutical composition. The method entails the compaction of a lyophilized or spray-dried pharmaceutical powder to obtain a densified material. The densified material can then be reground to produce compositions in which the individual particles approach the theoretical maximum density and are thus optimal for delivery by impact with and penetration into the target tissue at high velocities when delivered from a needleless syringe. In a particular embodiment, lyophilized recombinant human growth hormone (rhGH) powder is densified to obtain particles in the range of about 20 to 50 $\mu$m and having a bulk density of about 0.8 to 1.5 g/cc$^3$. The densified rhGH particles are ideally suited for delivery from a needleless syringe device.

In another embodiment, the invention is directed to a compacted particulate pharmaceutical composition formed from a porous pharmaceutical preparation. The compacted composition has an average particle size in the range of 0.1 to 250 $\mu$m mean diameter, a particle density in the range of 0.1 to 25 g/cm$^3$, and a bulk density of at least about 0.5 g/cc$^3$. Needleless syringes comprising the compacted particulate pharmaceutical preparation, as well as single-dose containers for a needleless syringe comprising the same, are also provided.

In another embodiment, the invention is directed to a method of delivering a selected pharmaceutical agent to a vertebrate subject. The method comprises providing a densified (compacted) particulate pharmaceutical preparation as described above and delivering the preparation to a target tissue of the vertebrate subject by needleless syringe.

In yet a further embodiment, the invention is directed to particles of a suitable size and density for transdermal delivery by needleless injection, consisting of a gene construct and an excipient selected from the group consisting of pharmaceutical grades of dextrose, sucrose, lactose, trehalose, mannitol, sorbitol, inositol, erythritol, dextrans, cyclodextrans, starch, cellulose, sodium or calcium phosphates, calcium sulfates, citric acid, tartaric acid, glycine, albumin, gelatin, polyacrylates, high molecular weight polyethylene glycols, and combinations thereof.

These and other embodiments of the subject invention will readily occur to those of skill in the art in light of the disclosure herein,

DETAILED DESCRIPTION OF THE PREFERRED EMBODIMENTS

The practice of the present invention will employ, unless otherwise indicated, conventional methods of molecular biology and recombinant DNA techniques within the skill of the art. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); DNA Cloning: A Practical Approach, vol. I & II (D. Glover, ed.); Perbal, A Practical Guide to Molecular Cloning.

Before describing the present invention in detail, it is to be understood that this invention is not limited to particular pharmaceutical formulations or process parameters as such may, of course, vary. It is also to be understood that the terminology used herein is for the purpose of describing particular embodiments of the invention only, and is not intended to be limiting.

It must be noted that, as used in this specification and the appended claims, the singular forms "a", "an" and "the" include plural referents unless the content clearly dictates otherwise. Thus, for example, reference to "a nucleic acid molecule" includes a mixture of two or more nucleic acid molecules, reference to "an excipient" includes mixtures of two or more excipients, and the like.

All publications, patents and patent applications cited herein, whether supra or infra, are hereby incorporated by reference in their entirety.

A. Definitions

Unless defined otherwise, all technical and scientific terms used herein have the same meaning as commonly understood by one of ordinary skill in the art to which the invention pertains. The following terms are intended to be defined as indicated below.

The term "transdermal" delivery captures both transdermal (or "percutaneous") and transmucosal administration, i.e., delivery by passage of a drug or pharmaceutical agent through the skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdermal Delivery of Drugs*, Vols. 1–3, Kydonieus and Berner (eds.), CRC Press, (1987). Aspects of the invention which are described herein in the context of "transdermal" delivery, unless otherwise specified, are meant to apply to both transdermal and transmucosal delivery. That is, the compositions, systems, and methods of the invention, unless explicitly stated otherwise, should be presumed to be equally applicable to transdermal and transmucosal modes of delivery.

By "needleless syringe" is meant an instrument which delivers a particulate composition transdermally, without a conventional needle that pierces the skin. Needleless syringes for use with the present invention are discussed throughout this document.

As used herein, the term "drug" or "pharmaceutical agent" intends any compound or composition of matter which, when administered to an organism (human or animal) induces a desired pharmacologic and/or physiologic effect by local and/or systemic action. The term therefore encompasses those compounds or chemicals traditionally regarded as drugs, vaccines, as well as biopharmaceuticals including molecules such as peptides, hormones, nucleic acids, gene constructs and the like. More particularly, the term "drug" or "pharmaceutical agent" includes compounds or compositions for use in all of the major therapeutic areas including, but not limited to, anti-infectives such as antibiotics and antiviral agents; analgesics and analgesic combinations; local and general anesthetics; anorexics; antiarthritics; antiasthmatic agents; anticonvulsants; antidepressants; antihistamines; anti-inflammatory agents; antinauseants; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins peptides and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like).

The above drugs or pharmaceutical agents, alone or in combination with other drugs or agents, are typically prepared as pharmaceutical compositions which can contain one or more added materials such as carriers, vehicles, and/or excipients. The terms "carriers," "vehicles" and "excipients" are used interchangeably herein and generally refer to substantially inert materials which are nontoxic and do not interact with other components of the composition in a deleterious manner. However, these terms do not encompass biolistic core carriers. The terms capture materials that can be used to increase the amount of solids in particulate pharmaceutical compositions, such as those prepared using spray-drying or lyophilization techniques. Examples of suitable carriers include water, silicone, gelatin, waxes, and like materials. Examples of normally employed "excipients," include pharmaceutical grades of dextrose, sucrose, lactose, trehalose, erythritol, dextrans, cyclodextrans mannitol, sorbitol, inositol, starch, cellulose, sodium or calcium phosphates, calcium sulfate, citric acid, tartaric acid, glycine, albumin, gelatin, polyacrylates high molecular weight polyethylene glycols (PEG), and combinations thereof.

"Gene delivery" refers to methods or systems for reliably inserting foreign DNA into host cells. Such methods can result in expression of non-integrated transferred DNA, extrachromosomal replication and expression of transferred replicons (e.g., episomes), or integration of transferred genetic material into the genomic DNA of host cells.

The nucleotide sequences are generally present in a suitable nucleic acid molecule and delivered in the form of vectors. By "vector" is meant any genetic element, such as a plasmid, phage, transposon, cosmid, chromosome, virus, virion, etc., which is capable of replication when associated with the proper control elements and which can transfer gene sequences between cells.

A "nucleotide sequence" or a "nucleic acid molecule" refers to DNA and RNA sequences. The term captures molecules that include any of the known base analogues of DNA and RNA such as, but not limited to 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

A "coding sequence" or a sequence which "encodes" a particular polypeptide, is a nucleic acid sequence which is transcribed (in the case of DNA) and translated (in the case of mRNA) into a polypeptide in vitro or in vivo when placed under the control of appropriate regulatory sequences. The boundaries of the coding sequence are conventionally determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and even synthetic DNA sequences. A transcription termination sequence will usually be located 3' to the coding sequence.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected gene is capable of being replicated, transcribed and translated in an appropriate recipient cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, or a nucleic acid molecule containing the nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

The term "transfection" is used to refer to the uptake of foreign DNA by a host cell, and a host cell has been "transformed" as a result of having been transfected. The foreign DNA may or may not be integrated (covalently linked) to chromosomal DNA making up the genome of the cell. By "host cell," or "host mammalian cell" is meant a cell which has been transfected, or is capable of being transfected, by a nucleic acid molecule containing a nucleotide sequence of interest. The term includes the progeny of the parent cell, whether or not the progeny is identical in morphology or in genetic make-up to the original parent, so long as the nucleotide sequence of interest is present within the cell.

By "biolistic core carrier" is meant a carrier on which a nucleic acid (e.g., DNA) is coated in order to impart a defined particle size as well as a sufficiently high density to achieve the momentum required for cell wall penetration, such that the DNA can be delivered using biolistic techniques, such as by use of a gene gun (see, e.g., U.S. Pat. No. 5,100,792). Biolistic core carriers typically include dense solids such as tungsten, gold, platinum, ferrite, polystyrene and latex. See e.g., *Particle Bombardment Technology for Gene Transfer*, (1994) Yang, N. ed., Oxford University Press, New York, N.Y. pages 10–11.

By "vertebrate subject" is meant any member of the subphylum cordata, particularly mammals, including, without limitation, humans and other primates. The term does not denote a particular age. Thus, both adult and newborn individuals are intended to be covered.

B. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

As explained above, the present invention allows for the highly efficient delivery of solid particles of nucleic acid molecules having a nominal average diameter of at least about 0.1 µm, preferably at least about 10 µm, to mammalian tissues. The method utilizes biolistic gene transfer techniques yet surprisingly allows for the delivery of nucleic acid molecules without the need for biolistic core carriers.

A wide variety of nucleic acid molecules can be delivered using the methods of the invention. Generally, the molecules contain coding regions with suitable control sequences or other therapeutically relevant nucleotide sequences. The nucleic acid molecules are prepared in the form of vectors which include the necessary elements to direct transcription and translation in a host cell. If expression is desired using the host's enzymes (such as by the use of endogenous RNA polymerase), the gene or genes will be present in the vectors operatively linked to control sequences recognized by the particular host, or even particular cells within the host. Thus, eucaryotic and phage control elements will be present for expression in mammalian hosts. Such sequences are known in the art and are discussed more fully below.

Suitable nucleotide sequences for use in the delivery methods of the present invention include any therapeutically relevant nucleotide sequence. Thus, the present invention can be used to deliver one or more genes encoding a protein defective or missing from a target cell genome or one or more genes that encode a non-native protein having a desired biological or therapeutic effect (e.g., an antiviral function). The invention can also be used to deliver a nucleotide sequence capable of providing immunity, for example an immunogenic sequence that serves to elicit a humoral and/or cellular response in a subject, or a sequence that corresponds to a molecule having an antisense or ribozyme function.

Suitable genes which can be delivered include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemia and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA that are useful in antisense therapy for cancer and for viral diseases have been described in the art. See, e.g., Han et al. (1991) *Proc. Natl. Acad. Sci. USA* 88:4313; Uhlmann et al. (1990) *Chem. Rev.* 90:543; Helene et al. (1990) *Biochim. Biophys. Acta.* 1049:99; Agarwal et al. (1988) *Proc. Natl. Acad. Sci. USA* 85:7079; and Heikkila et al. (1987) *Nature* 328:445. A number of ribozymes suitable for use herein have also been described. See, e.g., Cech et al. (1992) *J. Biol. Chem.* 267:17479 and U.S. Pat. No. 5,225,347 to Goldberg et al.

For example, in methods for the treatment of solid tumors, genes encoding toxic peptides (e.g., chemotherapeutic agents such as ricin, diphtheria toxin cobra venom factor), tumor suppressor genes such as p53, genes coding for mRNA sequences which are antisense to transforming oncogenes, antineoplastic peptides such as tumor necrosis factor (TNF) and other cytokines, or transdominant negative mutants of transforming oncogenes, can be delivered for expression at or near the tumor site.

Similarly, genes coding for peptides known to display antiviral and/or antibacterial activity, or stimulate the host's immune system, can also be administered. Thus, genes encoding many of the various cytokines (or functional fragments thereof), such as the interleukins, interferons, and colony stimulating factors, will find use with the instant invention. The gene sequences for a number of these substances are known.

For the treatment of genetic disorders, functional genes corresponding to genes known to be deficient in the particular disorder can be administered to the subject. The instant methods will also find use in antisense therapy, e.g., for the delivery of oligonucleotides able to hybridize to specific complementary sequences thereby inhibiting the transcription and/or translation of these sequences. Thus, DNA or RNA coding for proteins necessary for the progress of a particular disease can be targeted, thereby disrupting the disease process. Antisense therapy, and numerous oligonucleotides which are capable of binding specifically and predictably to certain nucleic acid target sequences in order to inhibit or modulate the expression of disease-causing genes are known and readily available to the skilled practitioner. Uhlmann et al. (1990) *Chem. Rev.* 90:543, Neckers et al (1992) *Crit. Rev. Oncogenesis* 3:175; Simons et al. (1992) *Nature* 359:67; Bayever et al. (1992) *Antisense Res. Dev.* 2:109; Whitesell et al. (1991) *Antisense Res. Dev.* 1:343; Cook et al. (1991) *Anti-Cancer Drug Design* 6:585; Eguchi et al. (1991) *Annu. Rev. Biochem.* 60:631. Accordingly, antisense oligonucleotides capable of selectively binding to target sequences in host cells are provided herein for use in antisense therapeutics.

For nucleic acid immunizations, antigen-encoding expression vectors can be delivered to a subject for the purpose of eliciting humoral and/or cellular immune responses to antigens encoded by the vector. In particular, humoral, cytotoxic cellular and protective immune responses elicited by direct intramuscular injection of antigen-encoding DNAs have been described. Tang et al. (1992) *Nature* 358:152; Davis et al. (1993) *Hum. Molec. Genet.* 2:1847; Ulmer et al. (1993) *Science* 258:1745; Wang et al. (1993) *Proc. Natl. Acad. Sci. USA* 90:4156; Eisenbraun et al. (1993) *DNA Cell Biol.* 12:791; Fynan et al. (1993) *Proc. Natl. Acad. Sci. USA* 90:12476; Fuller et al. (1994) *AIDS Res. Human Retrovir.* 10:1433; and Raz et al. (1994) *Proc. Natl. Acad. Sci. USA* 91:9519. In addition, these immune responses have also been elicited using biolistic techniques. See, e.g, EP 0500799.

Isolation of Genes and Construction of Vectors:

Nucleotide sequences selected for use in the present invention can be derived from known sources, for example, by isolating the same from cells containing a desired gene or nucleotide sequence using standard techniques. Similarly, the nucleotide sequences can be generated synthetically using standard modes of polynucleotide synthesis that are well known in the art. See, e.g., Edge et al. (1981) *Nature* 292:756; Nambair et al. (1984) *Science* 223:1299; Jay et al. (1984) *J. Biol. Chem.* 259:6311. Generally, synthetic oligonucleotides can be prepared by either the phosphotriester method as described by Edge et al. (supra) and Duckworth et al. (1981) *Nucleic Acids Res.* 9:1691, or the phosphoramidite method as described by Beaucage et al. (1981) *Tet. Letts.* 22:1859, and Matteucci et al. (1981) *J. Am. Chem. Soc.* 103:3185. Synthetic oligonucleotides can also be prepared using commercially available automated oligonucleotide synthesizers. The nucleotide sequences can thus be designed with appropriate codons for a particular amino acid sequence. In general, one will select preferred codons for expression in the intended host. The complete sequence is assembled from overlapping oligonucleotides prepared by standard methods and assembled into a complete coding sequence. See, e.g., Edge et al. (supra); Nambair et al. (supra) and Jay et al. (supra).

A particularly convenient method for obtaining nucleic acid sequences for use herein is by recombinant means. Thus, a desired nucleotide sequence can be excised from a plasmid carrying the same using standard restriction enzymes and procedures. Site specific DNA-cleavage is performed by treating with the suitable restriction enzyme (or enzymes) under conditions which are generally understood in the art, and the particulars of which are specified by manufacturers of commercially available restriction enzymes. If desired, size separation of the cleaved fragments may be performed by polyacrylamide gel or agarose gel electrophoresis using standard techniques.

Restriction cleaved fragments may be blunt ended by treating with the large fragment of *E. coli* DNA polymerase I (Klenow) in the presence of the four deoxynucleotide triphosphates (dNTPs) using standard techniques. The Klenow fragment fills in at 5' single-stranded overhangs but digests protruding 3' single strands, even though the four dNTPs are present. If desired, selective repair can be performed by supplying only one, or several, selected dNTPs within the limitations dictated by the nature of the overhang. After Klenow treatment, the mixture can be extracted with e.g. phenol/chloroform, and ethanol precipitated. Treatment under appropriate conditions with S1 nuclease or BAL-31 results in hydrolysis of any single-stranded portion.

PCR techniques can also be used in order to obtain a nucleic acid molecule of interest. Generally, the technique involves amplification of sequences from a human genomic or cDNA library. Degenerate or nondegenerate oligonucleotide primers for PCR may be prepared based on known amino acid sequences or on sequences of homologous genes. The products of such PCR reactions may be selected according to size by gel electrophoresis. Such PCR methods are described in e.g., U.S. Pat. Nos. 4,965,188; 4,800,159; 4,683,202; 4,683,195.

Once coding sequences for desired peptides or proteins have been prepared or isolated, such sequences can be cloned into any suitable vector or replicon. Numerous cloning vectors are known to those of skill in the art, and the selection of an appropriate cloning vector is a matter of choice. Ligations to other sequences are performed using standard procedures, known in the art.

Selected nucleotide sequences can be placed under the control of regulatory sequences such as a promoter, ribosome binding site and, optionally, an operator (collectively referred to herein as "control" elements), so that the sequence encoding the desired protein is transcribed into RNA in the host tissue transformed by a vector containing this expression construct. The coding sequence may or may not contain a signal peptide or leader sequence.

The choice of control elements will depend on the host being transformed and the type of preparation used. Thus, if the host's endogenous transcription and translation machinery will be used to express the proteins, control elements compatible with the particular host will be utilized. In this regard, several promoters for use in mammalian systems are known in the art and include, but are not limited to, promoters derived from SV40, CMV, HSV, RSV, MMTV, T7, T3, among others. Similarly, promoters useful with procaryotic enzymes are known and include the tac, spa, trp, trp-lac $\lambda$-$p_L$, T7, phoA promoters, as well as others.

In addition to control sequences, it may be desirable to add regulatory sequences which allow for regulation of the expression of protein sequences encoded by the delivered nucleotide sequences. Regulatory sequences are known to those of skill in the art, and examples include those which cause the expression of a coding sequence to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate control and, optionally, regulatory sequences such that the positioning and orientation of the coding sequence with respect to the control sequences allows the coding sequence to be transcribed under the "control" of the control sequences (i.e., RNA polymerase which binds to the DNA molecule at the control sequences transcribes the coding sequence). Modification of the sequences encoding the particular protein of interest may be desirable to achieve this end. For example, in some cases it may be necessary to modify the sequence so that it is attached to the control sequences with the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

Preparation of Particulate Molecules:

Once obtained and/or constructed, the nucleic acid molecules are prepared for delivery in particulate form. For example, particulate molecules can be produced using particle formation techniques well known in the art, such as but not limited to spray-drying, spray-coating, freeze-drying (lyophilization) and super critical fluid precipitation.

In one embodiment, the invention entails a procedure for forming dense particles from low density particulate pharmaceutical preparations. In particular, manufacturing processes for preparing pharmaceutical particles from delicate molecules such as DNA, proteins or peptides generally result in low density particles having either a hollow spherical or open lattice monolithic structure. Such particles are poorly suited for use in needleless syringe delivery systems, wherein the particles must have sufficient physical strength to withstand sudden acceleration to velocities approaching the speed of sound and the impact with, and passage through, the skin and tissue.

One common method of preparing particulate biopharmaceuticals, such as nucleic acids, is lyophilization (freeze-drying). Lyophilization relates to a technique for removing moisture from a material and involves rapid freezing at a very low temperature, followed by rapid dehydration by sublimation in a high vacuum. This technique typically yields low-density porous particles having an open matrix structure. Such particles are chemically stable, but are rapidly reconstituted (disintegrated and/or brought into solution) when introduced into an aqueous environment.

Another method of providing particulate preparations that can be used with these and other delicate or heat-sensitive biomolecules is spray-drying. Spray-drying relates to the atomization of a solution of one or more solids using a nozzle, spinning disk or other device, followed by evaporation of the solvent from the droplets. More particularly, spray-drying involves combining a highly dispersed liquid preparation (e.g., a solution, slurry, emulsion or the like) with a suitable volume of hot air to produce evaporation and drying of the liquid droplets. Spray-dried pharmaceuticals are generally characterized as homogenous spherical particles that are frequently hollow. Such particles have low density and exhibit a rapid rate of solution.

The low-density particulate solids produced by lyophilization and spray-drying techniques are ideal for redissolution for parenteral administration in solution via syringe or catheters. However, such particles are not useful for delivery from a needleless syringe in a solid form. Accordingly, for purposes of the present method, the preparations are densified to provide particles including nucleic acid molecules that are much better suited for delivery using a needleless syringe (e.g., substantially solid particles having a size of about 50 $\mu$m and a density of at least about 0.9 to 1.5 g/cc$^3$). In particular, the open lattice or hollow shell particles provided by spray-drying or lyophilization can be condensed without heating or shear to provide dense materials that can be milled or otherwise size-reduced to yield pharmaceutical particles having both size and density characteristics suitable for delivery by needleless injection.

The nucleic acids for delivery by the method of the invention, may be initially prepared in a formulation suitable for spray-drying or lyophilization. Such formulations generally require only a solution in which the nucleic acids will be stable for freezing and lyophilization and, optionally, an excipient for the drying procedure which is acceptable for parenteral delivery. In this regard, suitable excipients may be added to the formulations to provide sufficient mass for an individual dose, enabling measurement of doses by practical processes, e.g., by weight or volume. Typical dosages can be about 0.5 to about 5 mg, preferably about 1 to about 2 mg. Suitable excipients include, but are not limited to, carbohydrates (such as trehalose, glucose, dextrose and sucrose) or polyols (such as mannitol). Amino acids such as glycine and its hydrochloride salt can be used as buffers as well as phosphate, lactate or citrate buffers, among others. Additionally, any known composition for DNA stabilization will find use in the present formulations. The compositions may optionally include additive agents such as cryoprotectants, antioxidants, or the like. Adjusting compositions to enhance physical and chemical stability of the various particulate nucleic acid formulations provided herein is within the ordinary skill in the art.

One particular approach to stabilization during reprocessing of the nucleic acid formulations entails the use of additives which are combined with the solution prior to freezing for lyophilization to cause the nucleic acids to coil or ball and thus provide the genetic material as a discontinuous phase in the otherwise microscopically homogeneous particles. In such formulations, the bulking agent would be the continuous phase in the dried solid so that any grinding prior to compression, compression densification and regrinding (as described in detail below), and any particle attrition during sizing via sieve or air classification, acceleration and injection, would be less likely to disrupt the long chain nucleic acids. Homogeneity of the particles with respect to nucleic acid content is critical because of the potential for segregation by size during storage or injection.

Condensing the nucleic acid powders can be conducted by compaction in a suitable press (e.g., a hydraulic press, tableting press or rotary press), wherein the powders are compressed at about 1,000 to 24,000 pounds/square inch (e.g., 0.5 to 12 tons/square inch or 7 to 170 MPa) for a suitable time. Compaction can be carried out under vacuum if desired. The resulting compacted material is then coarsely reground until visually broken up. The particle size is then reduced to about a 20 to 50 $\mu$m average size with an optimal bulk particle density of around 0.9 to 1.5 g/cm$^3$, or as close to absolute or theoretical density as possible. Particle size reduction can be conducted using methods well known in the art including, but not limited to, roller milling, ball milling, hammer, air or impact milling, attrition milling, sieving, sonicating, or combinations thereof. The compression parameters and particle sizing will, of course, vary depending upon the starting material used, the desired target particle size and density, and like considerations.

Particle density can be ascertained using helium pycnometry to measure absolute density and various techniques to establish porosity such as mercury intrusion BET, flotation in a density gradient, and the like. These techniques are all well known in the art.

Thus, the method can be used to obtain nucleic acid particles having a size ranging from about 10 to about 250 $\mu$m, preferably about 10 to about 150 $\mu$m, and most preferably about 20 to about 60 $\mu$m; and a particle density ranging from about 0.1 to about 25 g/cm$^3$, and a bulk density of about 0.5 to about 3.0 g/cm$^3$, or greater.

A particularly preferred method for providing nucleic acid molecules suitable for biolistic delivery is the novel densification/compaction technique described herein. The technique is useful not only for preparing nucleic acid biopharmaceuticals, but can be used to prepare almost any desired physiologically active composition for needleless delivery.

Accordingly, in another embodiment of the invention, a method is provided for densifying (compacting) a non-nucleic acid pharmaceutical preparation.

As explained above, current manufacturing processes for preparing pharmaceutical particles from delicate molecules such as proteins or peptides are poorly suited for use in needleless syringe delivery systems. For example, as discussed above, lyophilization typically yields low-density porous particles having an open matrix structure. Exemplary biopharmaceuticals available as lyophilized particles include recombinant human growth factor (e.g., Genotropin®, Pharmacia, Piscataway, N.J.); somatrem (e.g., Protropin®, Genentech, S. San Francisco, Calif.); somatropin (e.g., Humatrope®, Eli Lilly, Indianapolis, Ind.); recombinant interferon $\alpha$-2a (e.g., Roferon®-A, Hoffman-La Roche, Nutley, N.J.); recombinant interferon $\alpha$-2b (e.g., Intron A®, Schering-Plough, Madison, N.J.); and recombinant alteplase (e.g., Activase®, Genentech, S. San Francisco, Calif.).

In addition, spray-dried pharmaceuticals are generally characterized as homogenous spherical particles that are frequently hollow. Such particles have low density and exhibit a rapid rate of solution. Exemplary heat-sensitive pharmaceuticals that are prepared using spray-drying techniques include the amino acids; antibiotics such as aureomycin, bacitracin, penicillin and streptomycin; ascorbic acid; cascara extracts; pepsin and similar enzymes; protein hydrolysates; and thiamine.

When spray-dried and lyophilized pharmaceutical particles are ground or milled, they yield very small, light and non-dense particles that are poorly suited for delivery through skin or mucosal tissues. In particular., such particles, when delivered from a needleless syringe, are often too light to have the momentum necessary to penetrate intact skin (e.g., pass through the stratum corneum) and would thus fail to enter the systemic circulation. In this regard, the stratum corneum is a thin layer of dense packed, highly keratinized cells, generally about 10–15 $\mu$m thick and which covers most of the human body. The stratum corneum thus provides the primary skin barrier which a transdermally-delivered particle must cross.

Accordingly, the present method entails densifying (compacting) such preparations to provide particles that are much better suited for delivery from a needleless syringe (e.g., substantially solid particles having a size of about 50 $\mu$m and a bulk density of at least about 0.5 to 1.5 g/cc$^3$). In particular, open lattice or hollow shell particles provided by spray-drying or lyophilization can be condensed without heating or shear to provide dense, compacted materials that can be milled or otherwise size-reduced to yield pharmaceutical particles having both size and density characteristics suitable for delivery by needleless injection.

Condensing of the spray-dried or lyophilized powders is typically conducted by compaction in a suitable press (e.g., a hydraulic press, tableting press or rotary press), wherein the powders are compressed at about 1,000 to 24,000 pounds/square inch (0.5 to 12 tons/square inch) for a suitable time. This compaction can be carried out under vacuum if desired. The resulting compacted material is then coarsely reground until visually broken up. The particle size is then reduced to about a 20 to 50 μm average size to yield a bulk density of around 0.5 to 1.5 g/cc$^3$ (with a particle density of about 0.1 to 25 g/cm$^3$). Particle size reduction can be conducted using methods well known in the art including, but not limited to, roller milling, ball milling, hammer or impact milling, attrition milling, sieving, sonicating, or combinations thereof. The compression parameters and particle sizing will, of course, vary depending upon the starting material used, the desired target particle size and density, and like considerations. The starting material can be any pharmaceutical preparation having a particle size and density which one is desirous of changing to obtain more optimal size and density characteristics for use in needleless syringes.

Following densification, particles of suitable size can be selected and classified using standard techniques, known in the art, such as by vibratory, sonic or jet sieving, cyclone separation, or like techniques, well known in the art.

Actual particle density, or "absolute density," can be readily ascertained using known quantification techniques such as helium pycnometry and the like. Alternatively, envelope density measurements can be used to assess suitable densification of the particulate pharmaceutical compositions. Envelope density information is useful in characterizing the density of porous objects of irregular size and shape. Envelope density, or "bulk density," is the mass of an object divided by its volume, where the volume includes that of its pores and small cavities. A number of methods of determining envelope density are known in the art, including wax immersion, mercury displacement, water absorption and apparent specific gravity techniques. A number of suitable devices are also available for determining envelope density, for example, the GeoPyc™ Model 1360, available from the Micromeritics Instrument Corp. The difference between the absolute density and envelope density of a sample pharmaceutical composition provides information about the sample's percentage total porosity and specific pore volume. In the practice of the invention, compaction of porous particulate pharmaceutical compositions will generally result in a reduction of porosity, and a concomitant increase in bulk (envelope) density.

Thus, the method can be used to obtain particles having a size ranging from about 0.1 to about 250 $\mu$m, preferably about 0.1 to about 150 $\mu$m, and most preferably about 20 to about 60 $\mu$m; a particle density ranging from about 0.1 to about 25 g/cm$^3$, and a bulk density of preferably about 0.5 to about 3.0 g/cm$^3$, and most preferably about 0.8 to about 1.5 g/cm$^3$.

The above-described method can also be used to optimize the density and particle size of a particulate pharmaceutical composition that has particle size and density characteristics that fall within the above ranges. In this manner, the penetration depths that are obtained when the optimized particles are delivered at high velocities using a needleless syringe can be adjusted to optimize targeted dermal or intra-dermal delivery.

However, as noted hereinabove, the invention is particularly suited for preparing densified particles having optimized density from heat-sensitive biopharmaceutical preparations of peptides, polypeptides, proteins, nucleic acids and other such biological molecules. Exemplary peptide and protein formulations which can be densified using the instant method include, without limitation, insulin; calcitonin; octreotide; endorphin; liprecin; pituitary hormones (e.g., human growth hormone and recombinant human growth hormone (hGH and rhGH), HMG, desmopressin acetate, etc); follicle luteoids; growth factors (such as growth factor releasing factor (GFRF), somatostatin, somatotropin and platelet-derived growth factor); asparaginase; chorionic gonadotropin; corticotropin (ACTH); erythropoietin (EPO); epoprostenol (platelet aggregation inhibitor); glucagon; interferons; interleukins; menotropins (urofollitropin follicle-stimulating hormone (FSH) and luteinizing hormone (LH)); oxytocin; streptokinase; tissue plasminogen activator (TPA); urokinase; vasopressin; desmopressin; ACTH analogues; angiotensin II antagonists; antidiuretic hormone agonists; bradykinin antagonists; CD4 molecules; antibody molecules and antibody fragments (e.g., Fab, $Fab_2$, Fv and sFv molecules); IGF-1; neurotrophic factors; colony stimulating factors; parathyroid hormone and agonists; parathyroid hormone antagonists; prostaglandin antagonists; protein C; protein S; renin inhibitors; thrombolytics; tumor necrosis factor (TNF); vaccines (particularly peptide vaccines including subunit and synthetic peptide preparations); vasopressin antagonists analogues; and $\alpha$-1 antitrypsin. Exemplary nucleic acid molecules are detailed above.

Administration of the Particles:

Following formation, the particulate preparations are delivered to mammalian tissue using a needleless syringe. The compacted particles of the present invention can be packaged in individual unit dosages. As used herein, a "unit dosage" intends a dosage receptacle containing a therapeutically effective amount of a pharmaceutical powder produced according to the methods of the present invention. The dosage receptacle is generally one which fits within a needleless syringe device to allow for transdermal delivery from the device. Such receptacles can take the form of capsules, foil pouches, sachets, cassettes, and the like. Appropriate needleless syringes are described herein above.

Transdermal delivery from these various needleless syringe configurations is carried out with particles having an approximate size that generally ranges between 0.1 and 250 $\mu$m. However, the optimal particle size is usually at least about 10 to 15 $\mu$m (the size of a typical cell). Particles larger than about 250 $\mu$m can also be delivered from the device, with the upper limitation being the point at which the size of the particles would cause untoward damage to the skin. Other particulate biopharmaceuticals, such as peptide and protein preparations, will generally have an approximate size of 0.1 to about 250 $\mu$m, preferably about 0.1 to about 150 $\mu$m, and most preferably about 20 to about 60 $\mu$m.

The actual distance which the delivered particles will penetrate depends upon particle size (e.g., the nominal particle diameter assuming a roughly spherical particle geometry), particle density, the initial velocity at which the particle impacts the skin surface, and the density and kinematic viscosity of the skin. In this regard, optimal particle densities for use in needleless injection generally range between about 0.1 and 25 g/cm$^3$, and optimal bulk densities range from about 0.5 and 3.0 g/cm$^3$. Injection velocities generally range between about 100 and 3,000 m/sec.

Compositions containing a therapeutically effective amount of the powdered molecules described herein can be delivered to any suitable target tissue via the above-described needleless syringes. For example, the compositions can be delivered to muscle, skin, brain, lung, liver, spleen, bone marrow, thymus, heart, lymph, is blood, bone cartilage, pancreas, kidney, gall bladder, stomach, intestine, testis, ovary, uterus, rectum, nervous system, eye, gland and connective tissues. For nucleic acid molecules, delivery is preferably to, and the molecules expressed in, terminally differentiated cells; however, the molecules can also be delivered to non-differentiated, or partially differentiated cells such as stem cells of blood and skin fibroblasts.

The powdered compositions are administered to the subject to be treated in a manner compatible with the dosage formulation, and in an amount that will be prophylactically and/or therapeutically effective. The amount of the composition to be delivered, generally in the range of from 0.5 µg/kg to 100 µg/kg of nucleic acid molecule per dose, depends on the subject to be treated. Doses for other pharmaceuticals, such as physiological active peptides and proteins, generally range from about 0.1 µg to about 20 mg, preferably 10 µg to about 3 mg.

The exact amount necessary will vary depending on the age and general condition of the individual to be treated, the severity of the condition being treated, the particular preparation delivered, the site of administration, as well as other factors. An appropriate effective amount can be readily determined by one of skill in the art.

Thus, a "therapeutically effective amount" of the present particulate compositions will be sufficient to bring about treatment or prevention of disease or condition symptoms, and will fall in a relatively broad range that can be determined through routine trials.

C. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

The following experiment was conducted to investigate the possibility of using freeze-dried DNA as an alternative to DNA-coated metal particles in the biolistic transfer of genetic material. In particular, powdered DNA plasmids as well as DNA-coated tungsten particles as controls were delivered ex vivo to male human fibroblast HT1080 cells using a needleless syringe apparatus as follows.

Clone 123 is a small plasmid of ~11 kb which contains the β-galactosidase marker gene so that transient transformation can be measured with the chromogenic indicator X-Gal. Plasmids were bulked with a carbohydrate excipient, trehalose. Trehalose was selected as the excipient because of its stabilizing properties (Colaco et al. (1992) Bio/Technology 10:1009). The trehalose was dissolved in distilled water and filter-sterilized prior to adding the DNA to the solution. Three different solutions of DNA sugar were made up with the proportions shown below in Table 1.

TABLE 1

| Preparation | 1 | 2 | 3 |
|---|---|---|---|
| Clone 123 (2.7 µg/µL) | 800 µg (296.3 µL) | 160 µg (59.3 µL) | 80 µg (29.6 µL) |
| Trehalose (100 mg/15 ml $H_2O$) | 10 mg (1.5 ml) | 10 mg (1.5 ml) | 10 mg (1.5 ml) |
| Payload (for 8 µg DNA) | 0.1 mg | 0.5 mg | 1.0 mg |

The plasmid/sugar solutions were then freeze-dried (using solid $CO_2$ and isopropanol to freeze the solution prior to vacuum drying), and the freeze-dried DNA-trehalose solid milled to form microparticles using an agate mortar and pestle.

As a control, DNA-coated tungsten particles were made by coating tungsten microprojectiles ($19.35 \times 10^3$ kb.m$^{-3}$) of 1.014 µm median diameter (M-17, GTE/Sylvania, Towanda, Pa., USA) with forty micrograms of Clone 123 plasmid DNA, giving five payloads of 8 µg DNA, using a derivative of known methods for coating microparticles. Potter et al. (1984) Proc. Natl. Acad. Sci. USA 81:7161, Klein et al. (1987) Nature 327:70, and Williams et al. (1991) Proc. Natl. Acad. Sci. USA 88:2726.

More particularly, prior to coating, the tungsten particles were sterilized and brought into suspension. A 50 mg sample of 1.048 µm (median diameter) tungsten microprojectiles (M-17, GTE/Sylvania, Towanda, PA, USA) was weighed into a 1.5 cc Eppendorf tube and then sterilized in 100% ethanol (EtOH). In order to disperse the microprojectiles (disrupt particle aggregates), the sterilized solution was sonicated thoroughly by contacting the outside of the Eppendorf tube with the probe of a sonicator. The dispersed tungsten particles were centrifuged and the supernatant removed. The tungsten particles were resuspended in 1 cc sterile distilled water and centrifuged for two cycles, and then stored in 1 cc sterile distilled water until coating.

The plasmid DNA was absorbed to the tungsten microprojectiles by adding 20 µL of the DNA (1 mg/mL) to 40 µL of the suspension of tungsten particles prepared above. The suspension was vortexed to ensure adequate mixing of the reagents. The following reagents were then added, in the order given, with vortexing after each addition: 253 µL $CaCl_2$ (2.5 M); 50 µL spermidine (0.10 M, stored frozen); and 207 µL sterile distilled $H_2O$. The final mixture was vortexed for 10 minutes at 4° C. The DNA-coated tungsten microprojectiles were then centrifuged at 500 G for 5 minutes. After centrifugation, all supernatant was carefully removed and 100 µL of 70% EtOH added. The coated particles were again centrifuged, all supernatant removed, and the final preparation resuspended in 30 µL of 100% EtOH.

The above method resulted in suitable quantities of DNA-coated tungsten particles to allow for 4 to 5 deliveries by the needleless syringe. The above-noted reagent quantities can, of course, be varied to provide different loadings of DNA in accordance with known methods. The volume and molar concentration (M) of the stock solutions used to coat tungsten with DNA are given below in Table 2.

TABLE 2

| Component | Quantity (µL) |
|---|---|
| Tungsten particles (50 mg/mL) | 40 |
| Clone 123 (2.7 µg/µL) | 14.8 |
| Ca $Cl_2$ (2.5M) | 253 |
| Spermidine (0.1M) | 50 |
| distilled $H_2O$ | 212.2 |

For transformation, 6 cm diameter culture dishes were seeded with $5 \times 10^5$ male human fibroblast HT1080 cells 24 hours before transfection. Two replicate dishes were prepared for each of the treatments, and two negative control plates were also prepared.

The microparticles and the tungsten-coated particles were then delivered to cells using a needleless syringe as described above. The syringe included a 4.5 mL reservoir chamber with plunger type valve, a helium gas reservoir, a Mach 2 nozzle and 12 μm Mylar sheet hand-punched into 6 mm diameter diaphragms.

In particular, mylar diaphragms were first sterilized by singly layering between pieces of filter paper, stacked one atop the other, wrapped in aluminum foil and sealed completely with autoclave tape to ensure that no water entered the filter paper/diaphragm stack during the autoclave process. This was placed inside a beaker covered with aluminum foil and placed in an autoclave chamber.

Two 12 μm Mylar diaphragms of 6 mm diameter were used in the membrane cassette. One milligram and one-half milligram payloads of the freeze-dried DNA powder were loaded onto the lower membrane in the cassette. This payload was then covered with the other pieces of the cassette and the remaining diaphragm. Only preparations 2 and 3 were used in the experiment because of the difficulty in weighing out small masses accurately. Another five of the cassettes were each loaded with 5 μL of the DNA/tungsten particle suspension. All the above quantities gave a mass of about 8 μg of DNA being delivered in each shot regardless of particle formulation used.

Figure 1:
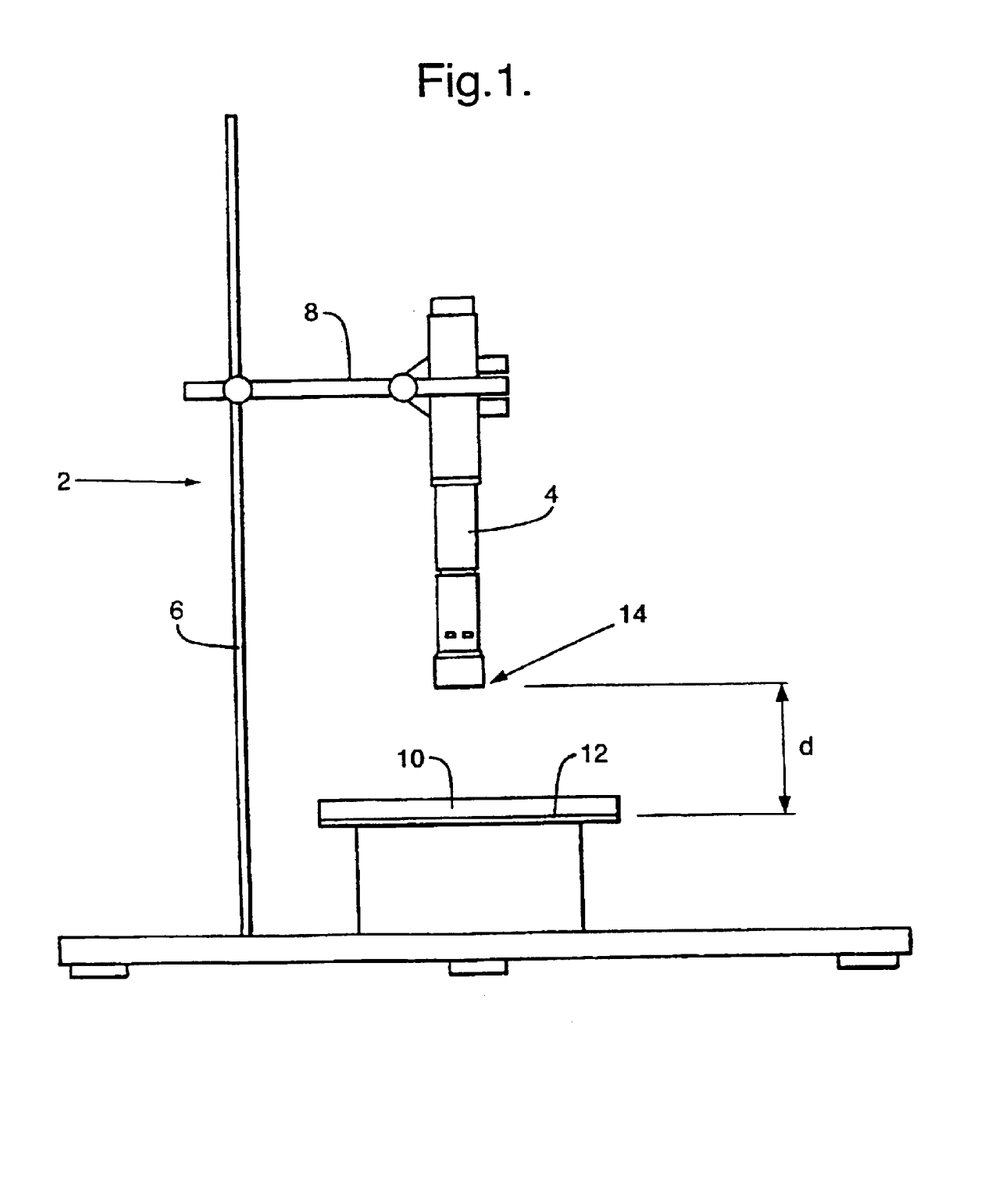
FIG. 1 is a pictorial representation of an ex vivo delivery apparatus having a needleless syringe arranged over a tissue culture plate containing cells to be transformed with the particulate nucleic acid preparations described herein.

Referring now to FIG. 1, a delivery apparatus 2 was assembled which contained a needleless syringe 4 loaded with a cassette as described above. The needleless syringe 4 was arranged on a ring stand 6 using a standard tube clamp 8 to hold the syringe in position relative to a culture dish 10 seeded with the HT1080 cells 12. The distance between the downstream terminus 14 of the needleless syringe 4 and the cells 14 in the culture dish 10 was measured to affix a target distance, generally indicated at d. In order to optimize the parameters for delivery of the freeze-dried DNA, either the target distance d was varied over a constant delivery pressure, or the delivery pressure was varied over a constant target distance. In particular, the DNA preparations were fired from a target distance ranging from 20 to 60 mm using helium driver gas pressures ranging from 30 to 50 bar.

After transformation, cells were incubated for 2 days, stained, and then transient assays with X-gal were performed to determine transformation efficiencies using previously described methods. Murray, E. J. (ed) (1991) *Methods in Molecular Biology: Gene Transfer and Expression Protocols*, Vol. 7, Humana Press, Clifton, N.J. Specifically, transformation efficiency was assessed by counting the number of blue-stained cells. The delivery parameters and transformation results are depicted below in Table 3. Blast effect was rated from 1 point for quite small (diameter of dead cell zone being approximately 5–8 mm) to five points for very large (diameter of cell zone being greater than 30 mm). As can be seen, transformation by the plasmid/trehalose powder preparation of the present invention was on the same order as that observed for the metallic particles.

Figure 2:
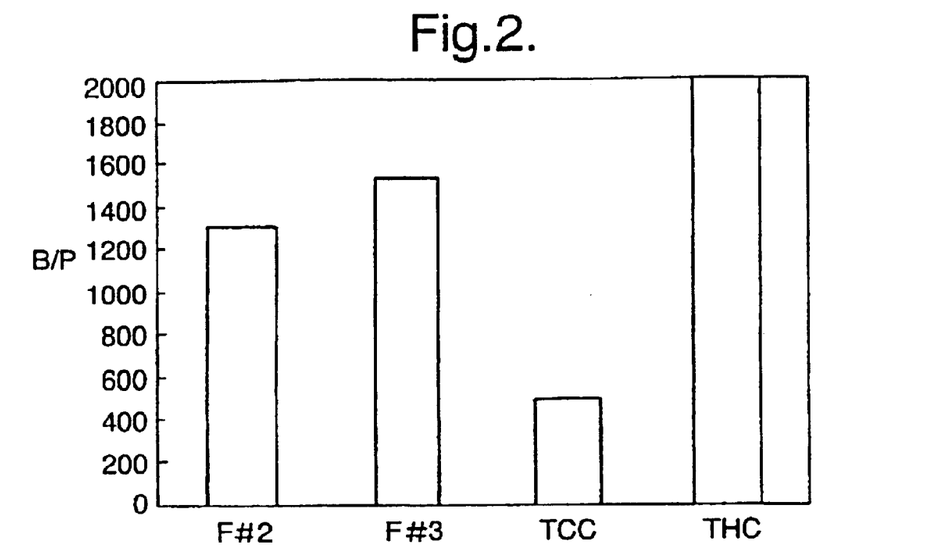
FIG. 2 is a histogram depicting transformation efficiencies obtained using the apparatus of FIG. 1 to deliver DNA particles at 30 bar pressure over a 60 mm target distance as described in Example 1. In the Figure, "B/P"refers to transformation efficiency (expressed as the number of blue cells/per culture dish), "F#2" and "F#3" refer to preparation 2 and preparation 3, respectively, "TCC" refers to the contemporaneous delivery of DNA-coated tungsten particles, and "THC" refers to a historical delivery of DNA-coated tungsten particles.
Figure 3:
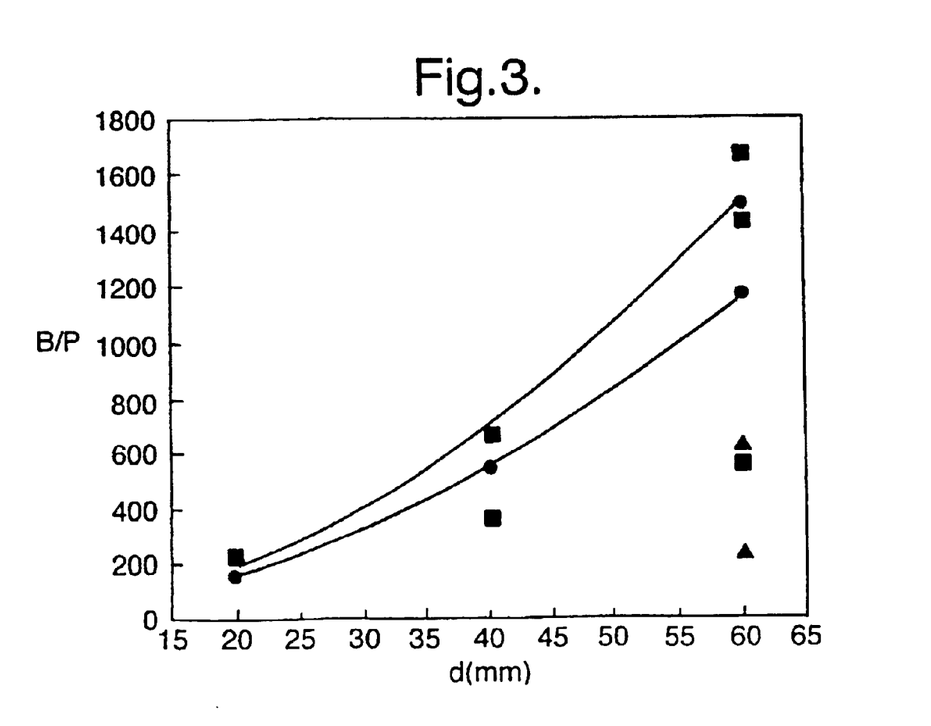
FIG. 3 is a graph depicting the transformation efficiencies obtained using the apparatus of FIG. 1 to deliver DNA particles at 30 bar pressure over a range of target distances, also as described in Example 1. In the Figure, "B/P" refers to transformation efficiency (expressed as the number of blue cells/per culture dish), and "d(mm)" refers to target distance expressed in mm.
Figure 4:
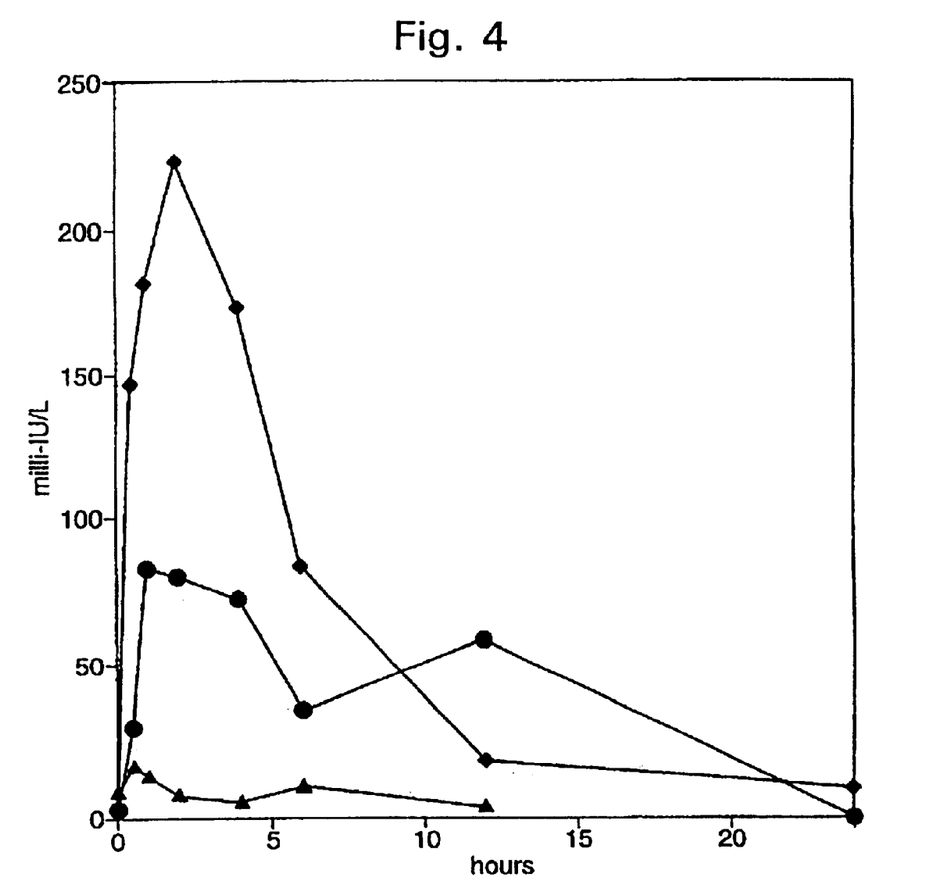
FIG. 4 depicts a comparison of the mean in vivo serum levels of recombinant human growth hormone (rhGH) in animals that were administered lyophilized rhGH powder by needleless injection (▲), densified rhGH particles (prepared by the method of the invention) by needleless injection (■), or lyophilized rhGH powder by sub-cutaneous injection (●).

As shown in FIG. 2, optimal transformation results were seen with the particulate plasmid/trehalose preparation when delivered using 30 bar pressure at a target distance of 60 mm. More particularly, FIG. 2 provides a direct comparison of the transformation efficiency obtained by delivery of the particulate nucleic acid preparation (both preparations 2 and 3) with historical and contemporary deliveries of DNA-coated tungsten particles. Referring now to FIG. 3, data obtained for deliveries at 30 bar are depicted in a graph which presents transformation efficiency as a function of target distance. As can be seen, the optimal target distance for the number 2 and 3 preparations (referred to as OBS Formulation #2 and OBS Formulation #3, respectively) was not reached; however, transformation efficiency did substantially increase with increased target distances. Further, when deliveries were carried out at the maximum distance tested (60 mm), transformation efficiencies obtained with the particulate DNA formulations (#2 and #3) were appreciably better than those observed with the DNA-coated tungsten controls.

TABLE 3

| Shot | Formulation | Target Distance | Pressure | Blue Cell Count | Blast effect |
|---|---|---|---|---|---|
| A1 | Tungsten | 60 | 30 | 224 | 2 |
| A2 | Tungsten | 60 | 30 | 596 | 2 |
| A3 | Tungsten | 60 | 30 | 575 | 2 |
| A4 | Tungsten | 60 | 30 | 581 | 2 |
| A5 | Tungsten | 60 | 30 | — | — |
| B1 | #3 trehalose | 20 | 30 | 155 | 3 |
| B2 | #3 trehalose | 20 | 30 | 227 | 3 |
| C1 | #3 trehalose | 40 | 30 | 654 | 2 |
| C2 | #3 trehalose | 40 | 30 | 643 | 2 |
| D1 | #3 trehalose | 40 | 50 | 394 | 4 |
| D2 | #3 trehalose | 40 | 50 | 175 | 5 |
| E1 | #3 trehalose | 60 | 30 | 1416 | 1 |
| E2 | #3 trehalose | 60 | 30 | 1654 | 1 |
| F1 | #3 trehalose | 60 | 50 | 408 | 3 |
| F2 | #3 trehalose | 60 | 50 | 486 | 3 |
| G1 | #2 trehalose | 20 | 30 | 166 | 3 |
| G2 | #2 trehalose | 20 | 30 | 180 | 3 |
| H1 | #2 trehalose | 20 | 50 | 129 | 4 |
| H2 | #2 trehalose | 20 | 50 | 53 | 4 |
| J1 | #2 trehalose | 40 | 30 | 347 | 2 |
| J2 | #2 trehalose | 40 | 30 | 546 | 2 |
| K1 | #2 trehalose | 40 | 50 | 377 | 4 |
| K2 | #2 trehalose | 40 | 50 | 198 | 4 |
| L1 | #2 trehalose | 60 | 30 | 1451 | 1 |
| L2 | #2 trehalose | 60 | 30 | 1164 | 1 |
| M1 | #2 trehalose | 60 | 50 | 409 | 3 |
| M2 | #2 trehalose | 60 | 50 | 336 | 3 |

Example 2

The following studies were carried out to assess the ability to deliver a powdered nucleic acid composition to test subjects in vivo using the methods of the invention.

Plasmid Vector Construct: The pGREEN-1 vector construct, which contains the Green Fluorescent Protein (GFP) gene under the control of a CMV promoter, was used so that gene expression could be assessed directly by UV microscopy of histological sections from treated tissue samples.

Powdered Nucleic Acid Compositions: A powdered nucleic acid composition was prepared as follows. A mixture was formed by combining pGREEN-1 vector plasmid with trehalose sugar to obtain a 1 μg:1 mg (w/w) DNA-sugar composition. This composition was lyophilized, compressed, ground, and then sieved, using the techniques described hereinabove. The resulting condensed nucleic acid composition had an average particle size ranging from about 38–75 μm.

Administrations: C57BL/10 mice were treated with 1 mg of the particulate composition via needleless injection. The composition was delivered to a suitably prepared target skin surface, and histological sections were taken from the target site 24 hours after administration. GFP expression was determined directly using UV microscopy. As a result of the administrations, GFP expression was seen in the treated skin tissue, confirming successful in vivo delivery of the powdered nucleic acid composition to the target skin, and the subsequent transfection of host cells and expression of the GFP gene therefrom.

In another study, plasmids containing either a human Growth Hormone (hGH) or β-galactosidase (β-Gal) expression cassette were lyophilized with trehalose excipient to form nucleic acid formulations, which were compressed, ground, and then sieved, using the above-described techniques. The resulting condensed nucleic acid compositions had an average particle size ranging from about 38–75 µm.

Female pigs (weighing 20–25 kg) were anesthestised with halothane, and the belly skin was clipped to reveal a suitable target site. The above powdered nucleic acid compositions were individually administered to the prepared target site in 0.1 µg (hGH) or 1 µg (β-Gal) doses via a needleless injection device (delivery pressure of 60 bar). The target sites were biopsied 24 hours after treatment, and histological sections were analyzed for human growth hormone or β-Gal expression. Although no hGH expression was seen within the detection limits of the assay, a moderate degree of β-Gal expression was seen in the treated sites. The lack of detectable hGH expression in this study is due, presumably, to the low loading density of the nucleic acid (0.1 µg) in the composition.

Example 3

Densification of Recombinant Human Growth Hormone (rhGH)

Lyophilized recombinant human growth hormone powder (Genotropin®, available from Pharmacia, Piscataway, N.J.) was obtained and reprocessed using the method of the invention. Particularly, approximately 30 mg of Genotropin was compacted under pressure using a Carver Laboratory Pellet Press (Model 3620, available from Carver, Inc., Wabash, Ind.). The pressure of compaction was 15,000 lbs/in$^2$, which was applied for approximately 45 seconds. A pellet was obtained which was ground using mortar and pestle until visually broken up. The resulting reduced pellet was then sieved using a 53 µm sieve (Endecott, London). Particles having a size greater than 53 µm were selected and appropriate dosages thereof were measured into drug cassettes for delivery from a needleless syringe.

Example 4

Visual Assessment of rhGH Particle Penetration

Lyophilized recombinant human growth hormone (rhGH) powder, and densified rhGH particles prepared as described in Example 3 were administered to porcine subjects using a needleless syringe. The degree of particle penetration was visually ascertained as follows.

Genotropin® 36 IU lyophilized powder was milled gently, weighed into individual doses of approximately 0.8 mg powder and loaded into a needleless syringe device for delivery. Densified Genotropin® was prepared as described in Example 3 and approximately 0.8 mg of the densified particles were loaded into a needleless syringe device for delivery.

Porcine subjects were prepared by clipping a sufficient area on the hindquarters. The lyophilized powder and densified particles were delivered to the porcine skin under high velocity. Upon a side-by-side comparison, it was observed that a higher proportion of the densified particles penetrated the skin as evidenced by the visual presence of the lyophilized powder remaining largely on the surface of the skin while substantially no densified particles were observed to remain on the surface of the skin.

Example 5

Serum Levels of Transdermally-Delivered rhGH

In order to determine the efficiency with which densified rhGH is delivered using a needleless syringe system, the following study was carried out. Three groups of 5 healthy New Zealand White rabbits were prepared by clipping the fur from the flank area to expose a sufficient area for delivery of lyophilized recombinant human growth hormone powder (rhGH) or densified rhGH by needleless syringe.

Approximately 0.8 mg of lyophilized Genotropin® powder was reconstituted into 1.8 mL of a suitable buffer without preservatives (e.g., sterile phosphate buffered saline (PBS)) to provide a Genotropin® solution having a concentration of 20 IU/mL. 1 mL dosages were withdrawn by syringe and gently mixed with 1 mL of buffer to provide an injection solution having a concentration of 10 IU/mL.

Each animal in the first group were given 0.1 mL/kg of the injection solution by subcutaneous needle and syringe injection, and the injection site was observed to ensure that there was no leakage of the injected solution after administration. Venous blood samples were taken from the marginal ear vein of the right ear of each animal at 0, 30 minutes, 1, 2, 4, 6, 12 and 24 hours after administration. Serum levels of rhGH were ascertained using an immunoassay with labeled anti-rhGH antibodies. The mean serum levels of subcutaneously delivered Genotropin® (●) found in the animals of Group 1 at each time point are depicted in FIG. 4.

Approximately 2 mg of lyophilized Genotropin® powder was loaded into a needleless syringe. The lyophilized powder was administered to each animal in the second group by needleless injection at high velocity. Venous blood samples were taken from the marginal ear vein of the right ear of each animal at 0, 30 minutes, 1, 2, 4, 6, 12 and 24 hours after administration. Serum levels of the administered rhGH were ascertained using an immunoassay with labeled anti-hGH antibodies. The mean serum levels of transdermally injected lyophilized Genotropin® powder (▲) found in the animals of Group 2 at each time point are depicted in FIG. 4.

Approximately 2 mg of densified Genotropin® particles prepared as in Example 3 was loaded into a needleless syringe. The densified particles were administered to each animal in the third group by needleless injection at high velocity. Venous blood samples were taken from the marginal ear vein of the right ear of each animal at 0, 30 minutes, 1, 2, 4, 6, 12 and 24 hours after administration. Serum levels of the administered rhGH were ascertained using an immunoassay with labeled anti-rhGH antibodies. The mean serum levels of transdermally injected densified Genotropin® particles (■) found in the animals of Group 3 at each time point are depicted in FIG. 4.

As can be seen, markedly increased blood serum levels of the densified Genotropin® particles administered by needleless syringe were obtained as compared to the lyophilized Genotropin® powder.

Example 6

Determination of Optimum Conditions for Needleless Syringe Delivery of rhGH

In order to determine optimum conditions for delivery of rhGH using a needleless syringe delivery system, the following study is carried out. One group of 8 healthy New Zealand White rabbits (2±0.25 kg) are prepared by clipping the fur from the flank area to expose a sufficient area for delivery of Lyophilized recombinant human growth hormone powder (rhGH) or densified rhGH by needleless syringe, sub-cutaneous (SC) or intravenous (IV) injection. The animals are weighed at the start of the study and on a weekly basis throughout the study to determine appropriate Genotropin® dosages. The animals remain in one large group to obtain statistically-significant data.

For an initial needleless syringe injection series, Genotropin® 36 IU lyophilized powder is milled gently and filled into a glass vial. The milled lyophilized powder is weighed into individual dosages and loaded into needleless syringe devices at approximately 0.8 mg powder/kg. The injection is conducted in the first week of the study, and multiple venous blood samples (1 mL whole blood) are taken from the marginal ear vein at times 0, 30 minutes, 1, 2, 4, 6, 12, 24 and 48 hours after administration. The animals are individually-housed at all times with food and water available ad libitum.

Blood samples are handled and processed as follows: each venous blood sample is allowed to clot at ambient temperature for approximately 30 minutes and then left for an additional 30 minutes at approximately 4° C. Clotted samples are centrifuged for 10 minutes and the serum is aspirated and stored at −20° C. for analysis.

In the second week of the study, (approximately 1 week following the initial needleless injection), the animals are administered a Genotropin® formulation prepared as follows: 36 IU (approximately 30 mg) of the lyophilized Genotropin® powder is reconstituted into 1.8 mL of a suitable buffer without preservatives (e.g., sterile phosphate buffered saline (PBS)) to provide a Genotropin® solution having a concentration of 20 IU/mL. 1 mL dosages are withdrawn by syringe and gently mixed with 1 mL of buffer to provide an injection solution having a concentration of 10 IU/mL. Each animal is given an IV injection of 0.1 mL/kg of the solution in the left ear.

Following IV injection, multiple venous blood samples are taken from the marginal ear vein of the right ear at times 0, 5, 10, 30 minutes, 1, 2, 4, 6 and 12 hours after injection.

In the third week of the study, the animals are administered 0.1 mL/kg of a buffered Genotropin® solution (prepared as above) by sub-cutaneous injection. The injection site is observed to ensure that there is no leakage after administration. Following the SC injections, multiple venous blood samples are taken from the marginal ear vein of the right ear at times 0, 30 minutes, 1, 2, 4, 6, 12, 24 and 48 hours after administration.

In the fourth week of the study, approximately 0.8 mg powder/kg of densified Genotropin® particles (prepared as described in Example 3) are administered to each animal using a needleless syringe, and multiple venous blood samples are taken from the marginal ear vein of the right ear at times 0, 30 minutes, 1, 2, 4, 6, 12, 24 and 48 hours after administration.

Serum rhGH levels are determined as previously described and pharmacokinetic variables are calculated for each drug administration technique. It is expected that needleless syringe administration of the densified Genotropin® particles will result in achieving and maintaining in vivo therapeutic levels of the administered drug.

Example 7

Bio-Activity of Densified rhGH Delivered In Vivo to Growth Hormone-Deficient Rats To evaluate the bio-activity of recombinant human growth hormone that has been densified using the method of the present invention the following study is carried out.

Dwarf or hypophysectomized (growth hormone-deficient) rats are administered pharmaceutical preparations containing either: densified Genotropin® particles; lyophilized Genotropin® powder; or placebo at approximately 4 IU rhGH per animal/week by daily sub-cutaneous (SC) injection. In particular, on 5 successive days, fur from the peritoneal region of the animal subjects is clipped prior to administration of the densified rhGH, the lyophilized rhGH or the placebo by SC injection. Body weight and, if desired, bone size and length are monitored on a daily basis.

Bio-activity of the densified rhGH particle formulation is determined by measuring body weight change over time. It is expected that the densified rhGH particle formulation will retain sufficient bio-activity.

Example 8

Densification of Commonly Used Excipients

Finely ground powders of pharmaceutical grade mannitol and lactose were obtained and reprocessed using the method of the invention. Particularly, approximately 30 to 50 mg of mannitol or lactose were compacted under pressure using a Carver Laboratory Pellet Press (Model 3620, available from Carver, Inc., Wabash, Ind.). The pressure of compaction was 10,000 lbs/in$^2$ which was applied for approximately 30 seconds. The resulting compacted pellets were ground using mortar and pestle until visually broken up, and then sieved to select for particles having a size greater than about 50 $\mu$m using the methods described in Example 3. In both the mannitol and the lactose preparations, a significant size reduction was observed when the compacted particles were compared against like weights of the non-densified starting materials.

Example 9

Quantification of Densified Excipients

Pharmaceutical grade trehalose and mannitol excipients were obtained and processed according to the method of the invention. Both excipient preparations were processed in several different ways, and absolute density, envelope density, and average particle size of the resultant preparations were measured as described below.

Trehalose 45H3830 (Sigma) and mannitol K91698380-703 (Merck) were either sieved, or freeze dried, compacted, ground and then sieved. A range of the resulting preparations were then analyzed for particle size and density measurements.

Portions of each sugar excipient were sieved to obtain preparations having reduced particle sizes. Sieving was carried out using stainless steel sieves for two hours at 3 mm amplitude using three sieve sizes (75 $\mu$m, 53 $\mu$m and 38 $\mu$m) without additional processing.

Alternatively, portions of each sugar excipient were processed using the methods of the invention as follows. 40 g of each of the sugars was dissolved in water, flash frozen, and then freeze dried over night. Samples of each freeze dried preparation were retained, and the remainder compacted in a 13 mm compression die (15,000 lbs/inch$^2$ for 45 seconds) into discs. The mannitol discs were ground using mortar and pestle, and then sieved as described above at 3 mm amplitude, using three sieve sizes. The trehalose discs were first ground in a vibratory ball mill (Retsch mill), then ground by mortar and pestle and sieved as above.

Samples from each of the above-described excipient preparations were then analyzed for absolute and envelope density. Absolute density was determined using helium pycnometry, and envelope density was determined using a GeoPyc™ Model 1360 Envelope Density Analyzer (Micromeritics Instrument Corp.). The results of the analysis are depicted below in Table 4.

TABLE 4

| Pretreatment | Trehalose Density (g/cm³) | | Mannitol Density (g/cm³) | |
| --- | --- | --- | --- | --- |
| | Absolute | Envelope | Absolute | Envelope |
| Sieved | 1.5 | 0.5 | 1.5 | 0.5 |
| Freeze Dried | 1.5 | 0.3 | 1.5 | 0.3 |
| Freeze Dried, Compressed, Milled, Sieved | 1.5 | 0.8 | 1.5 | 0.8 |

As can be seen in Table 4, none of the various processing methods had a significant effect on the absolute density of the powdered excipients. Further, as expected, the non-compacted, freeze-dried sugars had a much lower envelope density than the other preparations, and a concomitantly higher porosity (measurement not shown). The density measurements for the trehalose and mannitol samples clearly demonstrate that the methods of the invention (compression, milling, sieving) lead to a significant increase in envelope density relative to both the freeze-dried and the sieved preparations. These results indicate that the novel methods described herein can be used to provide densified particulate pharmaceutical preparations that are suitable for delivery via needleless injection techniques.

Accordingly, novel methods for DNA delivery as well novel methods for densifying particulate pharmaceutical compositions, and densified pharmaceutical compositions formed therefrom, have been described. Although preferred embodiments of the subject invention have been described in some detail, it is understood that obvious variations can be made without departing from the spirit and the scope of the invention as defined by the appended claims.

We claim:

1. A method for forming densified particles from a particulate pharmaceutical preparation, wherein the particulate pharmaceutical preparation is a preparation of a peptide or protein, the method comprising compacting the preparation in a press to provide a compacted pharmaceutical preparation and size-reducing the compacted preparation into densified particles of suitable size and density for transdermal delivery thereof by needleless injection.

2. A method according to claim 1, wherein the suitable size is in the range of about 0.1 to 150 $\mu$m mean diameter.

3. A method according to claim 2, wherein the suitable size is in the range of about 20 to 60 $\mu$m mean diameter.

4. A method according to claim 1, wherein the densified particles have a particle density in the range of about 0.5 to 3.0 g/cm³.

5. A method according to claim 4, wherein the particle density is in the range of about 0.8 to 1.5 g/cm³.

6. A method according to claim 1, wherein the particulate pharmaceutical preparation is a lyophilized or spray-dried composition.

7. A method according to claim 1, wherein compacting is carried out in a press at about 1,000 to 24,000 pounds per square inch.

8. A method according to claim 7, wherein compacting is carried out under vacuum.

9. A method according to claim 1, wherein compacting is carried out without heating or shear.

10. A method according to claim 1, wherein size reducing of the compacted material is carried out by milling, sieving, or a combination of milling and sieving.

11. A method according to claim 1, wherein the method further comprises selecting densified particles by size classification.

12. A method according to claim 11, wherein the size classification of the densified particles is carried out by sieving or cyclone separation.

* * * * *